US007208175B2

(12) United States Patent
Schroeder et al.

(10) Patent No.: US 7,208,175 B2
(45) **Date of Patent: *Apr. 24, 2007**

(54) PROCESS FOR THE PRODUCTION OF RAPIDLY DISINTEGRATING, SOLID PHARMACEUTICAL PREPARATIONS

(75) Inventors: Marco Schroeder, Schopfheim-Wiechs (DE); Klaus-Jürgen Steffens, Rheinbach (DE)

(73) Assignee: Bayer Ag, Leverkusen (DE)

( * ) Notice: Subject to any disclaimer, the term of this patent is extended or adjusted under 35 U.S.C. 154(b) by 35 days.

This patent is subject to a terminal disclaimer.

(21) Appl. No.: 10/600,409

(22) Filed: Jun. 19, 2003

(65) Prior Publication Data

US 2004/0057995 A1 Mar. 25, 2004

Related U.S. Application Data

(62) Division of application No. 10/030,456, filed on Jan. 3, 2002, now Pat. No. 6,602,520.

(51) Int. Cl.
*A61K 9/46* (2006.01)

(52) U.S. Cl. .......................... 424/466; 424/44; 424/465

(58) Field of Classification Search .................. 424/44, 424/440, 464–466, 485, 484, 488
See application file for complete search history.

(56) References Cited

U.S. PATENT DOCUMENTS

| | | | | |
|---|---|---|---|---|
| 1,450,865 | A | 4/1923 | Pele | 424/44 |
| 1,526,981 | A | 2/1925 | Heyl | 424/44 |
| 2,926,121 | A | 2/1960 | Hobbs et al. | 167/82 |
| 2,985,562 | A | 5/1961 | Millard et al. | 424/44 |
| 2,999,293 | A | 9/1961 | Taff et al. | 424/44 |
| 3,102,075 | A | 8/1963 | Millard | 424/44 |
| 3,653,914 | A | 4/1972 | Schmitt | 424/44 |
| 4,155,868 | A | 5/1979 | Kaplan et al. | 252/95 |
| 4,614,648 | A | 9/1986 | Bru | 424/44 |
| 4,678,661 | A | 7/1987 | Gergaly et al. | 424/44 |
| 4,946,684 | A | 8/1990 | Blanck et al. | 424/441 |
| 5,037,657 | A * | 8/1991 | Jones et al. | 424/466 |
| 5,302,396 | A | 4/1994 | Phadke et al. | 424/465 |
| 5,348,745 | A | 9/1994 | Daher | 424/466 |
| 5,354,742 | A | 10/1994 | Deming et al. | 514/117 |
| 5,437,873 | A | 8/1995 | Phadke et al. | 424/465 |
| 5,587,180 | A * | 12/1996 | Allen et al. | 424/499 |
| 5,609,883 | A | 3/1997 | Valentine et al. | 424/464 |
| 5,851,553 | A | 12/1998 | Myers et al. | 424/488 |
| 6,024,981 | A * | 2/2000 | Khankari et al. | 424/464 |
| 6,316,029 | B1 | 11/2001 | Jain et al. | 424/484 |
| 6,602,520 | B1 * | 8/2003 | Schroeder et al. | 424/466 |

FOREIGN PATENT DOCUMENTS

| | | |
|---|---|---|
| EP | 450141 B2 | 8/1990 |
| EP | 192460 B1 | 8/1991 |
| EP | 548356 B1 | 7/1992 |
| EP | 352190 B1 | 11/1992 |
| EP | 553777 A2 | 1/1993 |
| EP | 627218 B1 | 2/1993 |
| EP | 788891 A1 | 2/1996 |
| JP | A 08291051 | 11/1996 |
| WO | WO 98/29137 | 7/1997 |
| WO | WO 98/23656 | 11/1997 |
| WO | WO 98/46215 | 10/1998 |

* cited by examiner

*Primary Examiner*—Sreeni Padmanabhan
*Assistant Examiner*—Micah-Paul Young

(57) ABSTRACT

Rapidly disintegrating preparations containing at least one active pharmaceutical ingredient and at least one excipient can be obtained by a simple process in which at least the predominant part of the complete composition of the ingredients for the preparation to be produced is granulated, the resulting granules and, where appropriate, the remainder of the ingredients are shaped in the presence of liquid virtually without pressure, and the resulting shaped articles are dried.

6 Claims, No Drawings

PROCESS FOR THE PRODUCTION OF RAPIDLY DISINTEGRATING, SOLID PHARMACEUTICAL PREPARATIONS

This is a divisional application of U.S. Ser. No. 10/030,456, filed Jan. 3, 2002, now U.S. Pat. No. 6,602,520.

The invention relates to a process for the production of solid preparations which contain active pharmaceutical ingredient and rapidly disintegrate in aqueous liquids (such as, for example, water, saliva).

Pharmaceutical formulations which act immediately are required to disintegrate rapidly in liquids and quickly release the active ingredient. It is often attempted to achieve this aim by processing the active ingredient without binder but with excipients which promote disintegration of the preparations after the liquid gains access to give formulations such as, for example, tablets. However, satisfactory results are not obtained in all cases.

A new generation of pharmaceutical preparations which act immediately are expected to disintegrate and release the active ingredient in the shortest possible time. In addition, however, it would also be advantageous for the preparations to disintegrate in the presence of only small amounts of liquid, as are present, for example, on oral administration without addition of liquid, within a very short time without coarse granule particles remaining, which cause a "gritty feeling" in the mouth.

Effervescent preparations such as effervescent powders and effervescent tablets are a formulation form which can distinctly improve the disadvantageous properties of active ingredients when the active ingredients have a long absorption time and/or limited gastric tolerability. Pharmaceutical-containing effervescent preparations are therefore enjoying increasing popularity. It would therefore be desirable for the solution to be found to the problem also to be applicable to pharmaceutical effervescent preparations.

The required pharmaceutical preparations ought also to take appropriate account of the properties of the individual active ingredients such as, for example, the frequently encountered sensitivity to water. The solution to be found to the problem ought, of course, to lead to mechanically stable formulations (low friability, high hardness and compressive strength), which can be packaged without difficulty and can be stored and transported under usual conditions.

There have been diverse attempts to achieve this aim:

JP-A 08291051 discloses a process for producing tablets in which initially the active ingredients, water-soluble binder and water-soluble bulking agent are tabletted under very low pressure; the resulting tablets are then moistened and subsequently dried.

EP-A 192 460 describes tablets with a relatively hard shell of compressed material which is relatively resistant to liquids, there being rapid dissolution of the tablet ingredients after crushing of the tablet in the presence of liquid.

EP-A 352 190 describes the production of porous tablets which rapidly disintegrate in water and whose pores are produced by freeze drying a dispersion. The moulding composition for producing the tablets contains a defined amount of water to adjust the required viscosity.

EP-A 450 141 relates to a rapidly dissolving carrier material, inter alia for active pharmaceutical ingredients, with porous water-soluble, hydratable gel or foam material which has been hydrated with water, cured in the hydrated state and then dehydrated in such a way that cavities remain in place of the hydration liquid.

EP-B 548 356 discloses tablets containing disintegrating agents and/or swelling agents or soluble substances, where the (unpleasant-tasting) active ingredient is multiparticulate and is in the foam of coated microcrystals or coated microgranules.

EP-A 553 777 describes a process for producing porous, rapidly disintegrating tablets in which granules containing active ingredient and carbohydrate are moistened with water, and a tablet is shaped therefrom and dried. The dissolving times (in the mouth) are between 0.2 and 1.5 minutes.

U.S. Pat. No. 2,926,121 discloses a process for producing medicinal sweets in which sugar is added to a highly concentrated aqueous aluminium hydroxide suspension, a solid protective colloid is added to the resulting mixture, the mixture is homogenized and air is introduced, and the resulting pasty composition is allowed to dry at room temperature without exposure to heat.

U.S. Pat. No. 4,946,684 describes rapidly disintegrating tablets based on a matrix network structure composed of mannitol and a natural gum such as guar gum or gum acacia.

U.S. Pat. No. 5,851,553 describes a process for producing rapidly disintegrating tablets in which a mixture containing active ingredient and amorphous sugar is subjected to a so-called flash flow process where the sugar crystallizes in the form of a type of candyfloss. The candyfloss-containing voluminous composition can be shaped to tablets with small forces (preferably not more than 80 psi) and then subjected, where appropriate in a moist atmosphere, to a curing.

WO 98/23656 relates to a freeze-drying process for producing rapidly disintegrating tablets using lipids and structure-forming agents.

WO 98/29137 describes rapidly disintegrating tablets which comprise a solid dispersion of an active ingredient of low solubility in a gel-forming water-soluble polymer, and contain an alkali metal salt of a weak acid or of a strong acid with an endothermic standard dissolution enthalpy or dissolution heat.

WO 98/46215 discloses a technology in which granulation is dispensed with, and the active ingredients and a matrix containing a non-direct compression filler, for example mannitol, and a glidant are compressed to tablets. The tablets are intended to disintegrate quickly in the mouth and, during this, cause a minimal "gritty feeling".

It is furthermore known to make sucrose crystals slightly moist (residual moisture less than 2% by weight) and to follow compaction under high pressure by drying, resulting in porous but stable shaped articles.

The processes mentioned are either technically complicated or lead to products which do not have the expected short disintegration times or which have inadequate mechanical stability so that to protect from damage in some cases even special packaging techniques are proposed. Thus, whereas the known processes usually provide partial solutions for particular problems, there has to date been no economic process for preparations which meet all the above-mentioned requirements to a high degree.

It has now been found, surprisingly, that the stated object can be achieved by a technically very simple process.

The invention relates to a process for the production of preparations containing A) at least one active pharmaceutical ingredient and B) at least one excipient but—apart from an effervescent composition which is present where appropriate—no disintegrant, in which at least the predominant part of the complete composition of the ingredients for the preparation to be produced is granulated, the resulting granules and, where appropriate, the remainder of the ingredients are shaped in the presence of 2.5 to 15% by weight of liquid C), based on the total of solid ingredients and liquid, preferably water, ethanol and/or isopropanol, under a pressure of up to 100, preferably 0.1 to 50, in particular 1 to 20, $N/cm^2$ with a degree of compaction of 30 to 80%, based on moist complete composition to be shaped, and the resulting shaped articles are dried.

The solid preparations obtainable in this way are porous and are immediately moistened throughout on contact with aqueous liquid. The disintegration and the dissolution of preparations produced according to the invention and containing effervescent compositions take place virtually simultaneously within a few seconds. As a rule, disintegration and dissolution are complete within 2 to 12 sec, preferably within less than 8 sec, in particular within less than 5 sec (measured in a vessel charged with 150 ml of water at 20° C. or on the tongue without additional liquid being added); preparations produced according to the invention without effervescent compositions have completely disintegrated in this time and are at least one half dissolved.

The mechanical stability of the preparations obtainable according to the. invention makes transport, storage and handling possible without difficulty.

The term "active ingredient" comprises for the purpose of this invention active pharmaceutical ingredients in the narrower sense, that is to say preferably not foodstuffs (such as; for example, dairy products) and vitamins only in pharmaceutical dosage.

Preferred active ingredients A) for the preparations to be produced according to the invention are, for example,

- analgesics such as ibuprofen, ketoprofen, paracetamol, acetylsalicylic acid, $COX_2$ inhibitors such as nimesulide, meloxicam, naproxen, propyphenazone, metamizole,
- antacids such as hydrotalcite, magaldrate, calcium carbonate,
- antiasthmatics/bronchospasmolytics such as salbutarnol, tulobuterol, terbutaline, cromoglicic acid, ketotifen, theophylline,
- antibiotics such as quinolones, tetracyclines, cephalosporins, penicillins, macrolides, sulphonamides, polypeptides,
- psychopharmaceuticals such as benzodiazepines, haloperidol, amitriptyline, carbamazepine,
- antirheumatics such as phenylbutazone, indometacin, diclofenac, piroxicam,
- antidiabetics such as metformin, glibenclamide, acarbose, glisoxepide,
- antiallergics/antihistamines such as astemizole, terfenadine, loratadine, clemastine, bamipine, cetirizine,
- antihypotensives such as etilefrine, norfenefrine, dihydroergotamine mesilate,
- antitussives such as codeine, dextromethorphan, clobutinol, dropropizine,
- antihypertensives such as beta blockers such as propranolol, atenolol, metoprolol, prazosin,
- antihypertensives such as calcium channel blockers such as nifedipine, nitrendipine, diltiazem, verapamil, felodipine, nimodipine,
- laxatives such as sodium picosulphate, lactulose, lactitol,
- mucolytics/expectorants such as ambroxol, bromhexine, guaifenesin, acetylcysteine, carbocisteine,
- $H_2$ blockers such as ranitidine, famotidine, pirenzepine,
- local anaesthetics such as benzocaine, lidocaine, procaine,
- antiemetics/prokinetics such as metoclopramide, domperidone, meclozine, dimenhydrinate,
- lipid-lowering agents such as fenofibrate, bezafibrate, pravastatin, fluvastatin,
- agents effective for migraine, such as caffeine, dihydroergotamine, ergotamine, sumatriptan, pizotifen,
- sympathomimetics such as pseudoephedrine, pholedrine,
- vitamins and minerals.

In the case of active ingredients A) which are of low solubility per se it is generally advantageous to convert the active ingredients A) into water-soluble salts. Preferred water-soluble ASA salts comprise ASA lysinate and ASA arginate.

Further ingredients comprise

- carriers such as monosaccharides, for example glucose, oligosaccharides, for example sucrose, polysaccharides, for example maltodextrin and polyols, for example mannitol and sorbitol,
- binders such as glycine, maltodextrin, polyvinyl alcohol, polyvinylpyrrolidone, vinyl alcohol/vinylpyrrolidone copolymers, polyethylene glycol, ethylene oxide/propylene oxide mixed ethers, cellulose ethers, preferably hydroxypropylcellulose,
- wetting agents such as dioctyl sodium sulphosuccinate, sodium lauryl sulphate,
- lubricants such as polyethylene glycol, disodium fumarate,
- bulking agents such as highly disperse silica,
- vitamins and
- other pharmaceutical aids complying with the specifications in pharmaceutical textbooks.

The excipients B) are preferably water-soluble. "Water-soluble" in this sense means a solubility in water (20° C.) of at least 10, preferably at least 30 and, in particular, at least 40, g/100 ml of water. A particularly preferred excipient B) is maltodextrin.

The excipients B) furthermore comprise the effervescent composition necessary for effervescent preparations and containing (i) $CO_2$ donor and (ii) acidic component.

Preferred $CO_2$ donors (i) comprise alkali metal and alkaline earth metal carbonates and bicarbonates, in particular sodium and potassium carbonates and bicarbonates, and magnesium and calcium carbonates.

Suitable as acidic component (ii), which liberates carbon dioxide from the $CO_2$ donor (i), are all physiologically acceptable acids (so-called "acidulants") which are strong enough to liberate carbon dioxide from component (i); such acids have a first equilibrium exponent pKa of from 1 to 7, preferably from 2 to 6 (at 25° C). Preferred acidic components (ii) comprise ascorbic acid and polybasic carboxylic acids with 3 to 8, preferably 4 to 6, C atoms and 2 to 4 carboxyl groups per molecule, such as, for example, vitamin C, malic acid, citric acid, tartaric acid and mixtures thereof. Further preferred acidic components (ii) comprise the acidic salts of the abovementioned polybasic acids.

The effervescent composition preferably contains 30 to 70% by weight of $CO_2$ donor (i) and 70 to 30% by weight of acidic component (ii), in each case based on the total of the components (i) and (ii).

The shaped articles obtainable according to the invention should—apart from the effervescent composition which is present where appropriate—be free of so-called disintegrants (disintegrating aids). These include, for example, normal starch (such as corn or rice starch). It may be pointed out in this connection that the term "disintegrant" for a few substances such as, for example, starch also depends on the amount: whereas amounts of at least 5% by weight of starch (usually in powder form, that is to say avoiding contact with water), based on the finished shaped article, act as disintegrants, amounts of up to 3% by weight of starch, based on the finished shaped article, are used as binders in the granulation.

The term "disintegrant" comprises in particular the so-called superdisintegrants; these include a) crosslinked polyvinylpyrrolidone, which is normally employed in amounts of from 2 to 5% by weight, based on the finished shaped article; b) crosslinked carboxymethylcellulose ("croscar mellose sodium"), which is as a rule employed in amounts of from 2 to 5% by weight, based on finished shaped article; c) crosslinked starch, which is generally employed in amounts of from 2 to 10% by weight; and d) low-substituted hydroxypropylcellulose (L-HPC), which is normally employed in amounts of from 2 to 5% by weight, based on finished shaped article.

In a particular embodiment, the preparations produced according to the invention contain less than 3% by weight, based on finished shaped article, of swellable binders. "Swellable binders" in this sense are, in particular, natural starches, but not non-swelling water-soluble starches.

A particularly preferred preparation obtainable according to the invention contains an effervescent composition and A) acetylsalicylic acid and/or ibuprofen or water-soluble salts thereof and B) maltodextrin and/or mannitol.

Water is the most preferred liquid C). Suitable and preferred as liquid C) are also ethanol and isopropanol, and all conceivable mixtures which can be produced from at least two members of the group of water, ethanol and isopropanol.

The primary particles to be employed for the granulation should be as small as possible and, if possible, amorphous. The primary particle size of the active ingredients may vary within wide limits but will mostly be between 100 and 600, preferably 150 and 500, in particular less than 250, μm. The granulation can take place in a manner known per se on granulating plates, in granulating drums, in a fluidized bed or by vibration. Particularly porous granules can be obtained by prior reaction of the effervescent composition with water.

The uniformity and the speed of decomposition of the preparations produced according to the invention are promoted by a narrow particle size distribution of the granules. The preferred average particle diameter $d_{50}$ is 500 to 900 μm, where $d_{50}$ is the particle diameter above and below which in each case 50% by weight of the particles lie. The particle diameter $d_{10}$-$d_{90}$ is preferably in the range from 300 to 1300, in particular from 500 to 1000, μm. Because spherical granules provide an optimum in porosity and number of possible contact points, spherical and virtually spherical granules are preferred; a narrow particle size distribution is particularly preferred.

The liquid C) to be used according to the invention can be added before, during or after the granulation. Since the liquid C) acts as glidant in the shaping during the process according to the invention, other glidants can be dispensed with.

Undesirably large agglomerates can be removed by screening, for example by forced screening. The mesh width of the screen may vary within wide limits; as a rule it is from 0.5 to 2.0 mm, preferably 0.8 to 1.5 mm.

The residual moisture of the composition before the shaping can be 2.5 to 15, preferably 5 to 10, % by weight, based on the total of solid ingredients and liquid. It can be determined with a drying balance, for example with a Sartorius MA 40, at 50° C. Any water of crystallization present should not be taken into account in the moisture determination.

The apparent density of the granules is generally 0.5 to 1.8, preferably 0.7 to 1.5, g/cm$^3$.

The porosity of the granules can be 0.3 to 0.7, preferably 0.4 to 0.6.

The shaping can take place, for example, in tabletting machines (in order to avoid unwanted adhesion of the preparations to the die it is possible to coat the die with polytetrafluoroethylene because the die is exposed to only low forces). With tabletting machines and shaping compactors it is advisable for the shaped preparations to be ejected downwards.

The process according to the invention makes it possible to dispense with so-called lubricants or release agents. If, nevertheless, such agents are to be employed, very small amounts are sufficient, such as, for example, 0.001 to 0.2, preferably 0.03 to 0.1, % by weight, based on the moist composition before the shaping.

The compaction of the granules in moist form reduces to a minimum the work required for the shaping. The aim in the shaping should be a minimum of pressure applied.

For the shaping, a degree of compaction of from 30 to 80, preferably 55 to 70, in particular 60 to 65, %, based on the apparent density (moist) before the shaping, has proved suitable. The degree of compaction can be based on the height of the material poured into the die.

The true density of the preparations obtainable according to the invention (is calculated from the sample weight and the volume determined in helium (comparative gas pycnometer, for example Quantachrome Ultrapycnometer)) is generally 0.7 to 2.5, preferably 1.5 to 1.8, g/cm$^3$. The apparent density (determination of the shell volume in mercury (for example with a Pascal 440 Porosimeter from Carlo Erba) is calculated from the sample weight and the tablet volume (=solid volume+pore volume)) of the dried preparations produced according to the invention can be 0.2 to 1.8, preferably 0.5 to 1.5, g/cm$^3$, and their porosity (ratio of pore volume and tablet volume) can be 0.2 to 0.8, preferably 0.4 to 0.7, in particular 0.5 to 0.7.

Drying can take place by conventional methods, for example by contact, convection or radiation. Preferred dryers comprise tunnel dryers, circulating air tray chambers, vacuum dryers, infrared, microwave and high frequency equipment. The drying conditions depend on the size of the formulations. As a rule, temperatures of from 20 to 80° C., in the presence of effervescent composition of from 20 to 50° C., lead to good results. For example, circulating air drying at 40° C. is straightforward for most active ingredients. The drying times may be 10 minutes to 6 hours, preferably 0.5 to 4 hours. If necessary, the drying can be followed by a cooling step.

The hardness of the preparations produced according to the invention reaches values of from 10 to 110, preferably 20 to 50, N/cm$^2$, determined in a type 2E/205 hardness tester from Dr Schleuniger/Switzerland. This entails the force displayed by the measuring instrument being related to the fracture arca of the tablet which ideally breaks in the middle; thus, for a round tablet having a diameter of 20 mm and a height of 7 mm (fracture area 140 mm$^2$=1.4 cm$^2$), the hardness for a displayed force of 140 N is 140:1.4=100 N/cm$^2$.

If the active ingredients or excipients are hygroscopic or sensitive to air or light, this must be taken into account in the type of packaging.

Since the fast disintegration and the rapid release take place even with small amounts of liquid, the preparations produced according to the invention are also suitable for oral or rectal administration.

The percentages in the following examples are in each case based on weight; parts are parts by weight.

EXAMPLES

Example 1

2 g Effervescent Formulation with 500 mg of Active Ingredient Acetylsalicylic Acid (ASA)

A. Composition and Production 21.0 parts of sodium bicarbonate,
37.0 parts of sodium dihydrogen citrate,
29.4 parts of maltodextrin (DE 19), (DE=dextrose equivalent)
29.4 parts of acetylsalicylic acid and
0.8 part of dry orange flavour.

2000 g of a dry mixture of these substances were mixed for 15 minutes. The resulting mixture was rolled on a granulating plate under a fine spray of a total of 150 ml of demineralized water at room temperature; the resulting granules were then passed through a screen with a mesh width of 1.0 mm in order to remove large agglomerates.

The moist granules were then passed to a tabletting machine whose mould was coated with polytetrafluoroethylene. The maximum pressure was 64 N/cm$^2$, and the compaction was 62%. The ejected tablets (diameter 20 mm, height 7 mm) were then dried in a circulating air dryer at 38° C. for 3 hours. The tablets then had a hardness, measured in a type 2E/205 hardness tester from Dr Schleuniger/Switzerland, of 0.25 kg/cm$^2$.

B. Disintegration and Release Test in 150 ml of Water/20° C.

The tablet immediately sinks to the bottom, being moistened throughout. Within 2 to 5 sec, spontaneous disintegration is observed, with evolution of carbon dioxide, and the tablet fragments produced by the disintegration are driven to the surface. After 10 to 20 sec, measured from the introduction of the tablet into the water, dissolution of the tablet ingredients is complete.

Example 2

2.0 g formulation with active ingredient 500 mg of ASA lysinate (without effervescent composition)

Composition
49.0 parts of sodium citrate
60.0 parts of isomaltitol
90.0 parts of ASA lysinate
1.0 part of dry orange flavour

Example 3

1.6 g effervescent formulation with 200 mg of active ingredient ibuprofen lysinate Composition:
21.0 parts of sodium bicarbonate
37.0 parts of sodium dihydrogen citrate
33.7 parts of mannitol
25.1 parts of ibuprofen lysinate
0.8 part of dry orange flavour

Example 4

2.0 g of effervescent formulation with 600 mg of active ingredient acetylcysteine Composition:
21.0 parts of potassium bicarbonate
17.4 parts of sodium dihydrogen citrate
19.6 parts of sodium dihydrogen phosphate
23.5 parts of maltodextrin (DE 19)
35.3 parts of acetylcysteine
0.8 part of dry orange flavour

Example 5

1.5 g formulation with 50 mg of active ingredient diphenhydramine hydrochloride (without Effervescent Composition)

Composition:
39.0 parts of sodium citrate
105.0 parts of lactose (®Spherolac 100)
5.0 parts of diphenhydramine hydrochloride
1.0 part of dry orange flavour

Example 6

1.5 g formulation with 500 mg of active ingredient metamizole Sodium monohydrate Composition:
91.0 parts of maltodextrin
50.0 parts of metamizole sodium monohydrate
2.5 parts of aspartame
2.5 parts of acesulfame
4.0 parts of lemon flavour

The invention claimed is:

1. A process for making a fast-dissolve medicament comprising the steps of:

(a) preparing a combination comprising at least one active pharmaceutical ingredient, an effervescent couple and at least one excipient, other than the components comprising said effervescent couple, in the absence of a disintegrant, wherein at least the predominant part of the combination is granulated, to form a first mixture;

(b) tabletting said first mixture in the presence of 2.5 to 15% by weight of a liquid selected from the group consisting of water, ethanol, isopropanol and mixtures thereof at a pressure of up to 100 N/cm$^2$ with a degree of compaction of 30 to 80%, to form a porous effervescent tablet; and (c) drying said porous effervescent tablet.

2. The process of claim 1, wherein said active pharmaceutical ingredient is selected from the group consisting of analgesics, antacids, antiasthmatics/bronchospasmolytics, antibiotics, psychopharmaceuticals, antidiabetics, antiallergics/antihistamines, antihypotensives, antitussives, laxatives, mucolytics/expectorants, $H_2$ blockers, local anaesthetics, antiemetics/prokinetics, lipid-lowering agents, agents effective for migraine, and sympathomimetics and combinations thereof.

3. The process of claim 1, wherein the particle size of said first mixture is no larger than 2.0 mm.

4. The process of claim 1, wherein the residual moisture content of said porous effervescent tablet is from 5% to 10% before drying.

5. The process of claim 1, wherein said first mixture is tabletted at a pressure from 0.1 to 50 N/cm$^2$.

6. The process of claim 1, wherein said dried porous effervescent tablet has a porosity from 0.4 to 0.7.

* * * * *